United States Patent

Gardner et al.

[11] Patent Number: 5,540,682
[45] Date of Patent: Jul. 30, 1996

[54] ELECTROSURGERY APPARATUS

[75] Inventors: John A. Gardner, Steyning; Geoffrey P. Taylor, Findon; Kevin A. Hebborn, Hove; Razi Adelinia, Worthing, all of England

[73] Assignee: Smiths Industries Public Limited Company, London, England

[21] Appl. No.: 372,368

[22] Filed: Jan. 13, 1995

[30] Foreign Application Priority Data

Jan. 19, 1994 [GB] United Kingdom .................. 9400954

[51] Int. Cl.$^6$ .................................................. A61B 17/39
[52] U.S. Cl. ................................ 606/37; 606/39; 606/40
[58] Field of Search ......................................... 606/37–40

[56] References Cited

U.S. PATENT DOCUMENTS 5,290,283 3/1994 Suda .......................................... 606/37

FOREIGN PATENT DOCUMENTS

| 0194078 | 9/1986 | European Pat. Off. . |
| 0332308 | 9/1989 | European Pat. Off. . |
| 2133290 | 7/1984 | United Kingdom . |
| 2154881 | 9/1985 | United Kingdom . |

*Primary Examiner*—Lee S. Cohen
*Attorney, Agent, or Firm*—Pollock, Vande Sande & Priddy

[57] ABSTRACT

Electrosurgery apparatus has a processor that generates a data stream output representing the characteristics of the electrosurgery pulses to be generated. The data stream output comprises digitally-represented values indicative respectively of the width of each pulse, the duration of a first period during which pulses are to be generated, the duration of a second period during which pulses are not to be generated, the duration of a third period during which pulses are to be generated and the duration of a fourth period during which pulses are not to be generated. The data stream also includes digital instructions as to whether or not the electrosurgery output is to be cut only and whether it is to include spray coagulation. Three switch control units receive the data stream and provide outputs to three switching circuits, which provide two monopolar and one bipolar output. Each switching circuit includes a transformer connected to receive the outputs from the switch control units.

14 Claims, 3 Drawing Sheets

ELECTROSURGERY APPARATUS

BACKGROUND OF THE INVENTION

This invention relates to electrosurgery apparatus.

This invention is more particularly concerned with electrosurgery apparatus capable of performing different functions.

Electrosurgery apparatus includes a source of radio frequency power that is switched to give a pulsed output. The width, amplitude and separation between the pulses determines the surgical effect produced. Different surgical procedures, and different stages in a surgical procedure, require different electrosurgery outputs. For this reason, the apparatus is commonly arranged so that it can be switched between the different functions as desired. One way of producing the desired pulse pattern is to use a shift register having a number of memory locations each of which stores a binary signal representative of a pulse or a space between pulses. The output of the shift register is used cyclically to control the output of the apparatus, as described in EP-A-0194078.

BRIEF SUMMARY OF THE INVENTION

It is an object of the present invention to provide improved electrosurgery apparatus.

According to the present invention there is provided electrosurgery apparatus including means arranged to provide a data stream output comprising at least three separate, digitally-represented values indicative respectively of the width of each pulse, the duration of a first period during which the pulses are to be generated and the duration of a second period during which pulses are not to be generated, switch control means arranged to receive the data stream output and to provide a switching output in accordance therewith, and switching means arranged to receive the output of the switch control means and to provide a pulsed electrosurgery output in accordance therewith.

The data stream output may comprise at least four separate digitally-represented values including a value indicative of the duration of a third period during which pulses are to be generated after said first and second periods. The output may comprise at least five separate, digitally-represented values including a value indicative of the duration of a fourth period during which pulses are not to be generated after said first, second and third periods. Each of the digitally-represented values may comprise four bits. The data stream preferably includes a digital instruction as to whether or not the electrosurgery output is to be cut only and whether or not it is to include spray coagulation.

The switching means preferably includes a transformer with a primary and a secondary winding, the output of the switch control means including three signals on separate lines connected respectively to a center tapping of the primary and to opposite ends of the primary. The switching means may have a switching transistor connected between ground and each respective opposite end of the primary winding, the signals on lines connected to opposite ends of the primary winding controlling switching of the switching transistors. The switching means may include a resonant tank circuit, the signal supplied on the line connected to the center tapping being operable to connect the resonant tank circuit with the primary winding. The apparatus may include a plurality of switch control means and a plurality of respective switching means. At least one of the switching means preferably provides a monopolar output and another of the switching means provides a bipolar output.

Electrosurgery apparatus according to the present invention will now be described, by way of example, with reference to the accompanying drawings.

DETAILED DESCRIPTION OF THE PREFERRED EMBODIMENT

Figure 1:
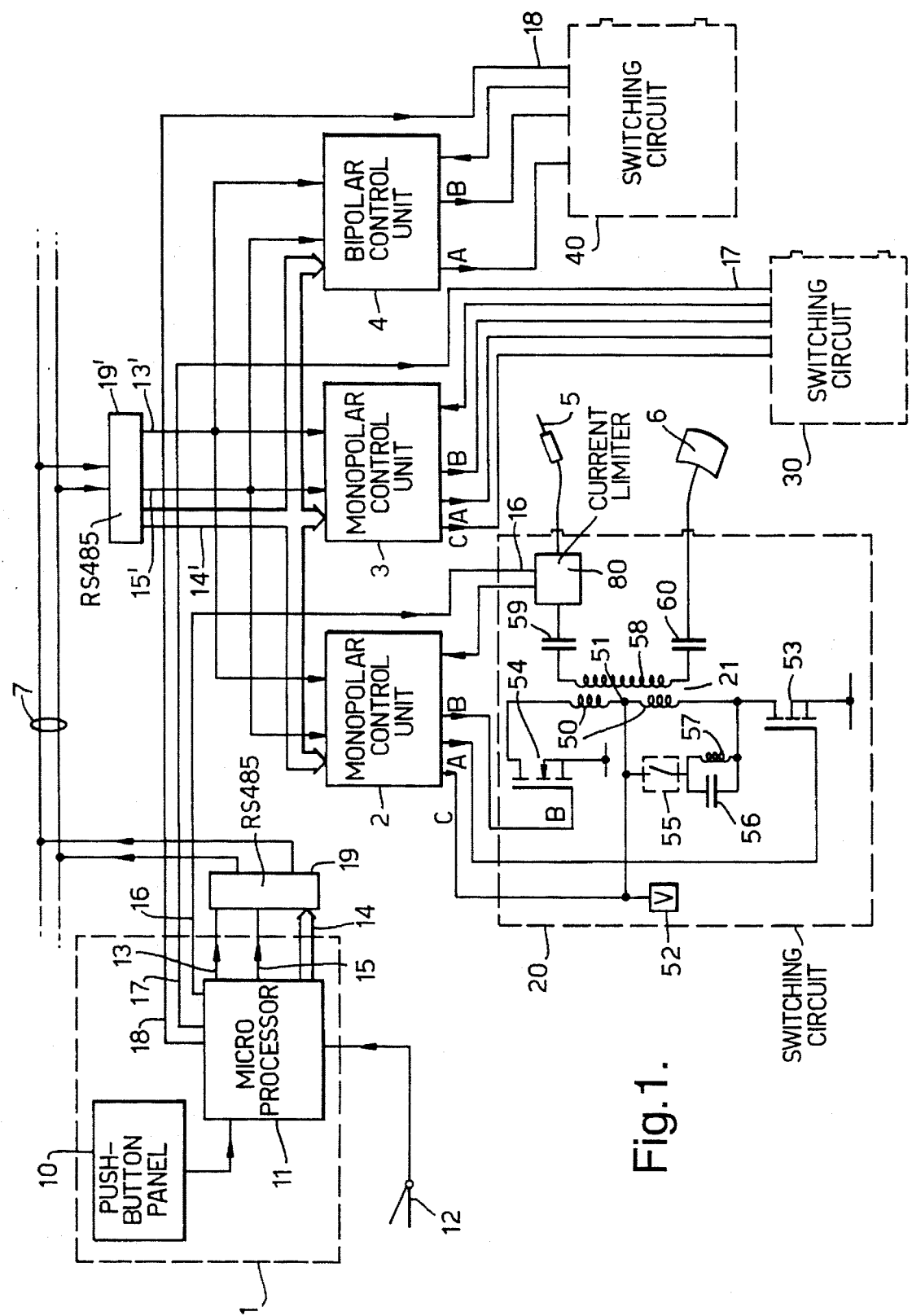
FIG. 1 shows the apparatus schematically.

With reference to FIG. 1, the apparatus comprises a control unit 1 that provides outputs to three switch control units 2, 3 and 4. Each of the switch control units 2 to 4 is connected to a respective output switching circuit 20, 30 and 40. Two of the circuits 20 and 30 provide an electrosurgery output to an active patient electrode 5 and a return electrode 6; the third circuit 40 provides a bipolar output.

The control unit 1 includes a user push-button panel 10, which the user operates to select the desired electrosurgery function, the main ones of which are: cut, blend (that is, cutting with some coagulation) and coagulation. The panel 10 also has buttons for the user to select monopolar or bipolar operation. The output from the push-button panel 10 is supplied to a microprocessor 11, which also receives an input from various different manually-operated switches, such as a finger switch or footswitch 12.

The microprocessor 11 generates several sets of outputs when the footswitch 12 or other manually-operated switch is actuated. One output, on line 13 is a data clock signal. A second output on line 14 is a 4-bit address that selects one of the three different switch control units 2, 3 or 4. A third output on line 15 is a 24-bit serial data stream giving information as to the pulse width and the time periods for duration of the pulses and gaps between the pulses. More particularly, the 24-bits of the datastream are allocated as follows: the first four bits 0–3 digitally represent the time of the first period for generation of pulses; the second four bits 4–7 represent the time of the off period following the first pulse generation period; the third four bits 8–11 represent the time of the second period for generation of pulses; the fourth four bits 12–15 represent the time of the off period following the second pulse generation period; the fifth four bits 16–19 represent the width of each pulse; the twenty-first bit 20 is used to instruct whether or not the electrosurgery output is to be cut only; the twenty-second bit 21 is used to instruct whether spray coagulation is to be included; the twenty-third bit 22 is a parity bit; and the final bit 23 is unused. The microprocessor 11 also generates three enable signals on lines 16, 17 and 18, which are supplied to respective ones of the switching circuits 20, 30 or 40. The enable signals are produced in response to actuation of the footswitch 12 or other user-controlled switch.

The signals on lines 13 to 15 are supplied to a RS485 serial communicator circuit 19, which converts the inputs into serial data outputs on a two-wire bus 7. The bus 7 extends throughout the apparatus and is used for control of other functions of the apparatus. Connection is made to the bus 7 in the vicinity of the switch control units 2 to 4 by an input circuit 19' that converts the signals on the bus into signals corresponding to those supplied to the communicator circuit 19 and supplies these on output lines 13', 14' and 15' to the switch control units 2, 3 and 4. The enable signals on lines 16, 17 and 18 are supplied to the switching circuits 20, 30 and 40 independently of the bus 7.

The monopolar switch control units 2 and 3 provide three outputs A, B and C whereas the bipolar control unit 4 provides two outputs A and B when selected by the user. The switch control units 2 to 4 are driven by the datastream output on line 15 from the control unit 1 and provide the pulsed outputs encoded in the datastream. The pulsed output of the activated control unit 2, 3 or 4 is supplied to its associated switching circuit 20, 30 or 40. Each switching circuit 20, 30 or 40 includes a transformer 21 with a primary coil 50 having a center tapping 51 connected to a voltage source 52. Opposite ends of the coil 50 are connected to ground via respective switching transistors 53 and 54, which are controlled by the outputs on line A and B respectively. The output C is connected to a switch 55 in series between the center tapping 51 and one end of a resonant tank circuit comprising a capacitor 56 and inductor 57 connected in parallel. The other end of the tank circuit is connected to the node between the switching transistor 53 and the coil 50. The output of the switching circuits 20 and 30 are taken from a secondary coil 58 and two isolating capacitors 59 and 60 to the active and return electrodes 5 and 6. The output from the bipolar switching circuit 40 is similarly supplied to the bipolar electrodes.

Figure 2:
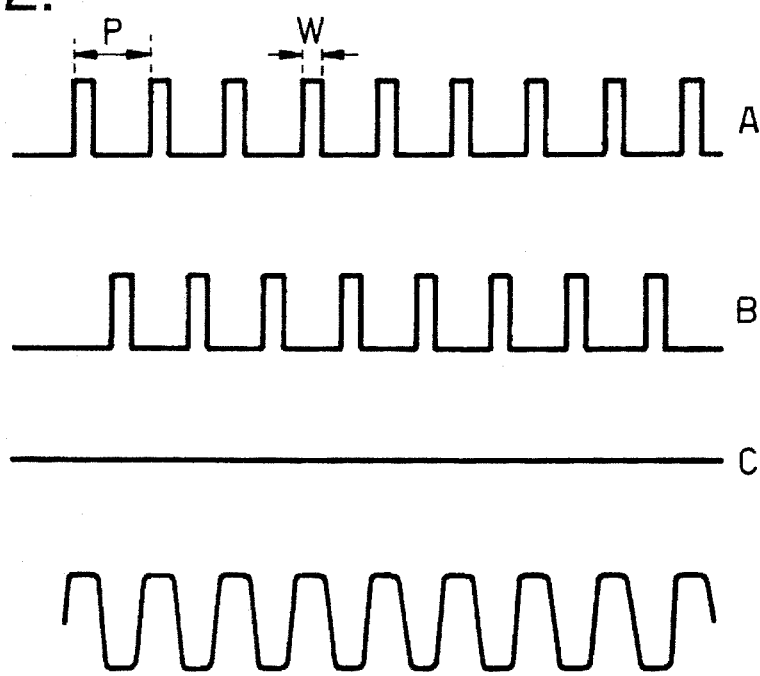
FIGS. 2 to 5 illustrate different outputs of the apparatus.

The manner in which the different electrosurgery pulse patterns are produced will now be described with reference to FIGS. 2 to 5. FIG. 2 shows inputs to the switching circuit 20 or 30 necessary to give the cut mode produced by the continuous oscillating wave output shown in the bottom line of the Figure. To produce this pattern the C output is off or low so that the switch 55 is off or open. The A output consists of regularly repeating pulses separated by spaces of constant time. Typically, the period P between pulses is about 2 μs and the width W of the pulses is less than or equal to 1 μs. The B output is identical to A except that it is out of phase by 180°. When one of the A pulses is applied to the switching circuit 20 or 30 it renders the switching transistor 53 conductive and allows current to flow through the lower half of the primary coil 50. This induces a current in the secondary coil 58. When one of the B pulses is applied to the switching circuit 20 or 30 it closes the other switching transistor 54 and allows current to flow in the opposite direction through the upper half of the primary coil 50. This induces a current in the secondary coil 58 of opposite polarity from that produced by the A pulses. The combined effect of the antiphase A and B pulses, therefore, is to produce the full wave signal illustrated in the bottom line.

Figure 3:
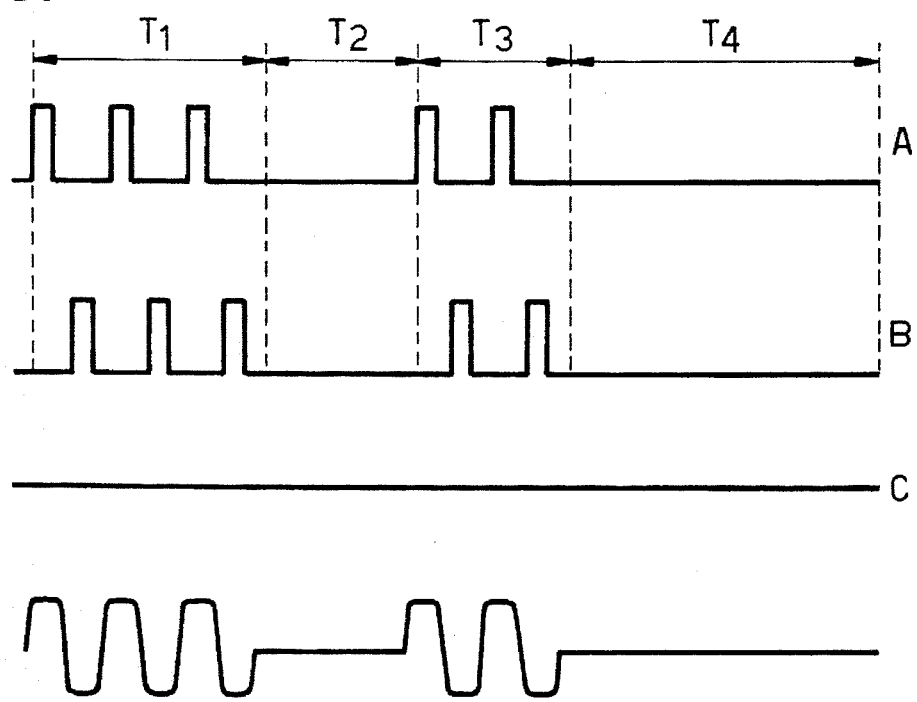

A blend output is produced by the pulses shown in FIG. 3. The A output consists of two groups of pulses separated by intervals without pulses. The first group of three pulses occurs over a first time period $T_1$. This group is separated by an off period of duration $T_2$ before the second group of pulses. The second group of pulses consists of two pulses over a period $T_3$ and is followed by a second off period $T_4$ before the first group is repeated again. The B output is again identical to the A output but is in antiphase with it so that a full-wave oscillating output is produced consisting of two bursts of different duration separated by gaps of different duration.

Figure 4:
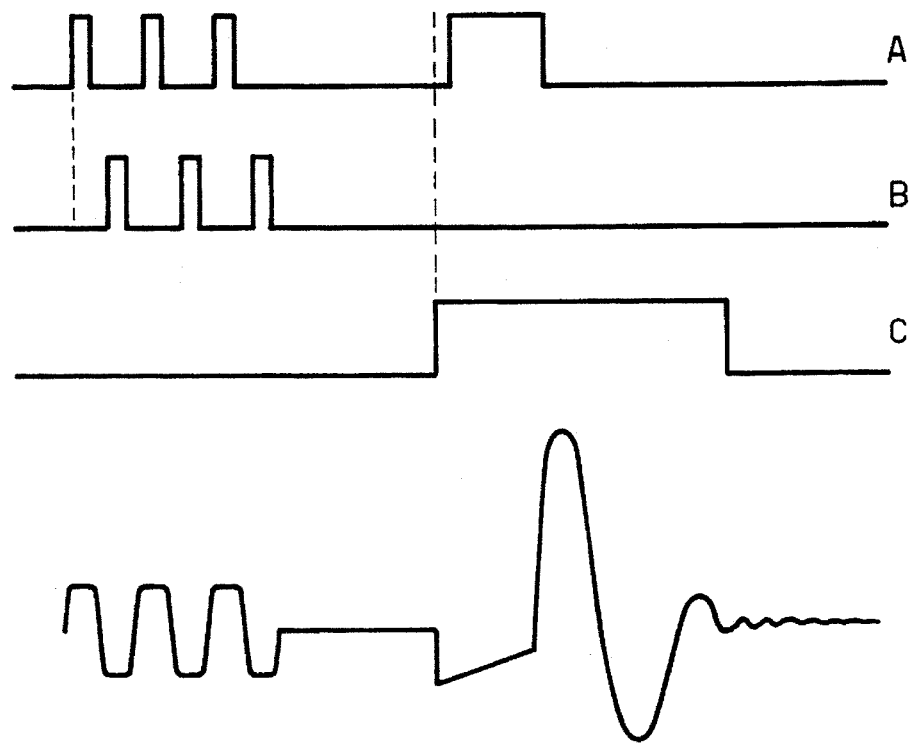

A combined blend and spray coagulation output is produced by the pulses shown in FIG. 4. The A output consists of a first group of three pulses followed by an off period identical to that shown in FIG. 3. The second pulse group, however, differs from that of FIG. 3 in that it consists of a single pulse of increased width, as signalled by the twenty-second bit 21 in the datastream. This is followed by an off period until the first pulse group reoccurs. The B output is an antiphase version of the A output but does not have any second pulse group. An output is also produced on line C, just prior to the start of the second pulse group A, this output consisting of a single pulse that continues until about halfway through the second off period in the A output. The effect of the C pulse is to close the switch 55 and place the resonant tank circuit, formed by the capacitor 56 and the inductor 57, in parallel with the lower half of the primary coil 50. When the transistor 53 is closed by a long pulse in the A output, the tank circuit is charged at the same time as current flows through the lower half of the primary coil 50. At the end of the pulse in the A output, the transistor 53 opens but the switch 55 remains closed for a time determined by the remaining duration of the pulse in the C output. This produces a positive resonant pulse followed by a negative resonant pulse as the tank circuit discharges. This process continues until all the energy in the tank circuit has decayed but the voltage generated across the decaying tank circuit ceases to be applied across the primary coil 50 before decay is completed because the switch 55 is opened before then. The resultant waveform output consists of an initial group of pulses followed by a gap similar to that of the blend waveform. This is followed by a negative-going pulse which reduces in negative value and is followed by an initially high amplitude oscillating signal that is highly damped.

Figure 5:
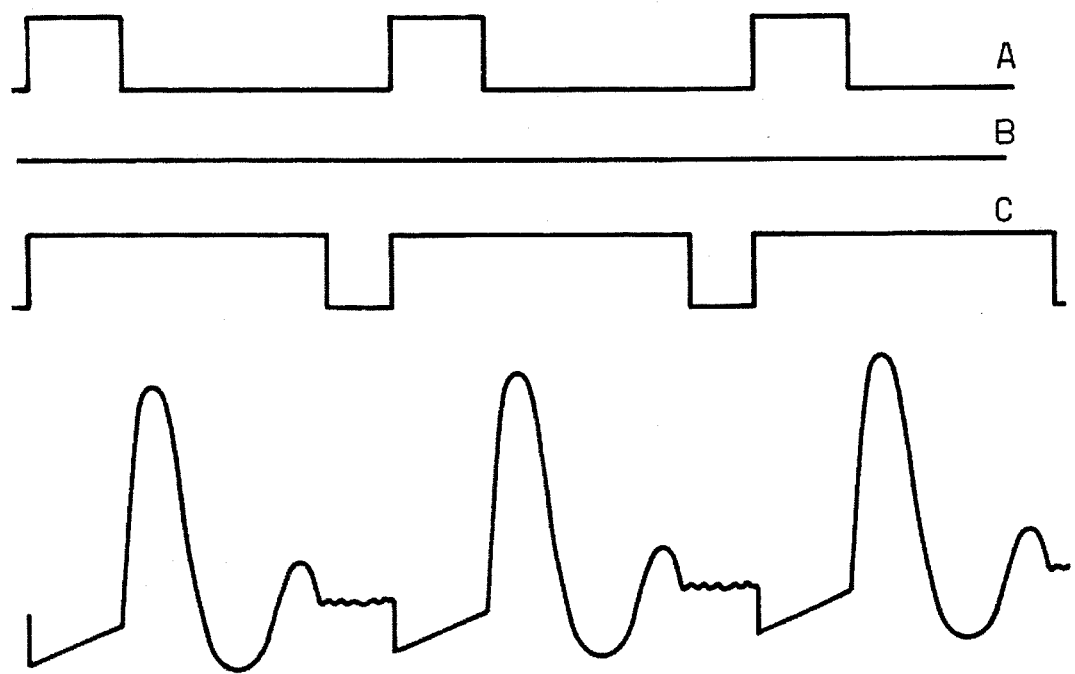

An electrosurgery output that is entirely spray coagulation is produced by the pulses shown in FIG. 5. The spray coagulation pulse streams can be of any length. In the present example, the A output consists of three, relatively wide positive pulses equally spaced from one another by spaces larger than the pulse width. Longer spray coagulation pulses can be produced by increased numbers of pulses in the A output. The C pulses are also positive and are initiated just before the A pulses but are of longer duration, being separated from one another by spaces that are short compared with the duration of the pulses This produces three high amplitude, damped tinging signals of the same kind as the second group of signals in the combined blend with spray coagulation signal shown in FIG. 4.

In use, while the user holds the footswitch 12 depressed, the microprocessor 11 supplies enable signals via lines 16 to 18 to the current limiting device 80, with which the enable signals are AND gated. As long as current flow is below an upper safe limit and the enable signal is received by the current limiting device, the output from the current limiting device 80 to the switch control unit 2, 3 or 4 will be such as to enable an electrosurgery output to be produced. If, however, the footswitch 12 should be released, so that the enable signal ceases, or an excessive current should flow, the current limiting device 80 would produce an inhibit output to its associated switch control unit 2, 3 or 4. This would have the effect of terminating the electrosurgery output at the end of the current pulse stream. The current limiting device 80 resets relatively quickly and reapplies current without the user noticing that the output has been interrupted. The switching of the current keeps the average current below the upper safe limit.

When used with a bipolar electrode, that is, one in which the active and return electrodes are closely spaced from one another in a hand-held device, the bipolar electrode is connected to the bipolar control unit 4, via its output switching circuit 40. Because bipolar electrodes cannot operate in the spray mode, the control unit 4 does not produce any C output and the output switching circuit 40 lacks the capacitor, inductor and switch used in the other switching circuits 20 and 30.

The apparatus can readily be arranged to produce different forms of output such as specialist cut or pin-point coagulation. The apparatus of the present invention can operate flexibly and with reliability.

What we claim is:

1. Electrosurgery apparatus for providing a pulsed electrosurgery output, said apparatus comprising: a processor, said processor providing a data stream output comprising at least three separate, digitally-represented values indicative respectively of the width of each pulse, the duration of a first period during which the pulses are to be generated and the duration of a second period during which pulses are not to be generated; a switch control unit; means connecting said switch control unit to said processor so that said switch control unit receives the data stream output and provides a switching output in accordance therewith; a switching circuit; a voltage source; means connecting the switching circuit to said switch control unit so that said switching circuit receives the switching output of the switch control unit; and means connecting said voltage source to said switching circuit so that said pulsed electrosurgery output is produced by switching of said switching circuit.

2. Electrosurgery apparatus according to claim 1, wherein the data stream output comprises at least four separate, digitally-represented values including a value indicative of the duration of a third period during which pulses are to be generated after said first and second periods.

3. Electrosurgery apparatus according to claim 2, wherein the data stream output comprises at least five separate, digitally-represented values including a value indicative of the duration of a fourth period during which pulses are not to be generated after said first, second and third periods.

4. Electrosurgery apparatus according to claim 1, wherein each of the digitally-represented values comprises four bits.

5. Electrosurgery apparatus according to claim 1, wherein the data stream output includes a digital instruction as to whether or not the electrosurgery output is to be cut only.

6. Electrosurgery apparatus according to claim 1, wherein the data stream output includes a digital instruction as to whether or not the electrosurgery output is to include spray coagulation.

7. Electrosurgery apparatus according to claim 1, wherein the switching circuit includes a transformer, said transformer having a primary winding and a secondary winding, and wherein the means connecting the switch control unit to the switching circuit includes three separate lines connected respectively to a center tapping of the primary winding and to opposite ends of the primary winding.

8. Electrosurgery apparatus according to claim 7, wherein the switching circuit includes a switching transistor connected between ground and each respective opposite end of said primary winding, and wherein signals on said lines connected to opposite ends of the primary winding control switching of said switching transistors.

9. Electrosurgery apparatus according to claim 7 or 8, wherein the switching circuit includes a resonant tank circuit, and wherein the signal supplied on said line connected to said center tapping is operable to connect the resonant tank circuit in circuit with said primary winding.

10. Electrosurgery apparatus according to claim 1, wherein the apparatus includes a plurality of switch control units and a plurality of respective switching circuits.

11. Electrosurgery apparatus according to claim 10, wherein at least one of said switching circuits provides a monopolar output and another of said switching circuits provides a bipolar output.

12. Electrosurgery apparatus for providing a pulsed electrosurgery output, said apparatus comprising: a processor, said processor providing a data stream output comprising at least three separate, digitally-represented values indicative respectively of the width of each pulse, the duration of a first period during which pulses are to be generated and the duration of a second period during which pulses are not to be generated; a switch control unit; means connecting said switch control unit to said processor so that said switch control unit receives the data stream output and provides at least two switching outputs in accordance therewith; a switching circuit, said switching circuit including a transformer having a secondary winding and a primary winding and two switching transistors connected between ground and respective opposite ends of said primary winding; a voltage source; means connecting said voltage source to a center tapping of said primary winding; and means connecting the switching circuit to said switching transistors so that two pulsed signals are applied across the primary winding to produce said pulsed electrosurgery output across said secondary winding in accordance therewith.

13. Electrosurgery apparatus according to claim 12, wherein the switch control unit provides three outputs, wherein the switching circuit includes a resonant tank circuit and a switch operable to connect the tank circuit with the primary winding, and wherein a third output of said switch control unit is connected to said switch to control connection of the tank circuit with the primary winding.

14. Electrosurgery apparatus for providing a pulsed electrosurgery output, said apparatus comprising: a processor, said processor providing a data stream output comprising at least five separate, digitally-represented values indicative respectively of the width of each pulse, the duration of a first period during which the pulses are to be generated, the duration of a second period during which pulses are not to be generated, the duration of a third period during which pulses are to be generated and the duration of a fourth period during which pulses are not to be generated, and two further digital instructions as to whether or not the electrosurgery output is to be cut only and whether or not the electrosurgery output is to include spray coagulation; a switch control unit; means connecting said switch control unit to said processor so that said switch control unit receives the data stream output and provides a switching output in accordance therewith; a switching circuit; a voltage source; means connecting the switching circuit to said switch control unit so that said switching circuit receives the output of the switch control unit; and means connecting said voltage source to said switching circuit so that said pulsed electrosurgery output is produced by switching of said switching circuit.

* * * * *